(12) United States Patent
Wu et al.

(10) Patent No.: US 9,675,428 B2
(45) Date of Patent: Jun. 13, 2017

(54) VIDEO-BASED AUTO-CAPTURE FOR DENTAL SURFACE IMAGING APPARATUS

(71) Applicant: Carestream Health, Inc., Rochester, NY (US)

(72) Inventors: Yingqian Wu, Shanghai (CN); Yufeng Mo, Shanghai (CN); Qinran Chen, Shanghai (CN); Victor C. Wong, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 40 days.

(21) Appl. No.: 14/326,568

(22) Filed: Jul. 9, 2014

(65) Prior Publication Data

US 2015/0017598 A1    Jan. 15, 2015

Related U.S. Application Data

(60) Provisional application No. 61/845,440, filed on Jul. 12, 2013.

(51) Int. Cl.
*A61C 9/00* (2006.01)
*A61B 5/00* (2006.01)
*G01B 11/25* (2006.01)

(52) U.S. Cl.
CPC ............ *A61C 9/006* (2013.01); *A61B 5/0088* (2013.01); *A61B 5/4547* (2013.01);
(Continued)

(58) Field of Classification Search
CPC .................. G01N 21/8806; G01N 2021/4742
(Continued)

(56) References Cited

U.S. PATENT DOCUMENTS 5,372,502 A    12/1994  Massen et al.
5,604,817 A *   2/1997  Massen .................... A61C 9/00
                                                        356/602
(Continued)

FOREIGN PATENT DOCUMENTS

EP        2 756 793 A1    7/2014
WO    WO 2011/145799 A    11/2011

OTHER PUBLICATIONS

International Search Report mailed on Nov. 6, 2014 for International Application No. PCT/US2014/046061, 2 pages.

(Continued)

*Primary Examiner* — Kara E Geisel
*Assistant Examiner* — Shawn Decenzo

(57) ABSTRACT

In an exemplary method for obtaining a contour image of a tooth, which can be executed at least in part by a computer, movement of an intra-oral camera can be detected by acquiring a first video image frame that includes the tooth and processing the first video image frame to detect one or more edges of the tooth in the first video image frame and acquiring a second video image frame that includes the tooth and processing the second video image frame to detect the one or more edges of the tooth in the second video image frame. The method can compare corresponding edge locations between the first and second processed video image frames and projects a fringe pattern illumination onto the tooth from the camera, capturing and storing one or more still images of the fringe pattern according to the detected camera movement.

16 Claims, 15 Drawing Sheets

(52) U.S. Cl.
CPC .......... *G01B 11/2518* (2013.01); *A61B 5/004* (2013.01); *A61B 2576/00* (2013.01)

(58) Field of Classification Search
USPC ................................ 356/601–614, 375, 457
See application file for complete search history.

(56) References Cited

U.S. PATENT DOCUMENTS

| | | | |
|---|---|---|---|
| 6,532,299 | B1 | 3/2003 | Sachdeva et al. |
| 6,885,464 | B1 | 4/2005 | Pfeiffer et al. |
| 7,312,924 | B2 | 12/2007 | Trissel |
| 7,702,139 | B2* | 4/2010 | Liang .................. A61B 1/0638 382/128 |
| 2006/0127836 | A1* | 6/2006 | Wen ................................ 433/24 |
| 2007/0086762 | A1 | 4/2007 | O'Keefe et al. |
| 2010/0158490 | A1 | 6/2010 | Pfeiffer et al. |
| 2010/0198566 | A1* | 8/2010 | Lauren ................. A61C 9/0053 703/1 |
| 2012/0062716 | A1 | 3/2012 | Dillon et al. |
| 2014/0294273 | A1* | 10/2014 | Jaisson ................ A61B 5/7425 382/131 |
| 2015/0348320 | A1* | 12/2015 | Pesach ................. A61C 9/0033 382/128 |

OTHER PUBLICATIONS

Ming-Yu Liu, et al., "Fast Directional Chamfer Matching," Proceedings of the IEEE Conference on Computer Visions and Pattern Recognition (CVPR'10), San Francisco, California, Jun. 2010, 8 pages.

\* cited by examiner

VIDEO-BASED AUTO-CAPTURE FOR DENTAL SURFACE IMAGING APPARATUS

CROSS REFERENCE TO RELATED APPLICATIONS

This application claims the benefit of U.S. Provisional application U.S. Ser. No. 61/845,440, provisionally filed on Jul. 12, 2013, entitled "AN APPARATUS OF VIDEO-BASED AUTO-CAPTURE FOR INTRA-ORAL CAMERA", in the names of Yingqian Wu et al., incorporated herein in its entirety.

TECHNICAL FIELD

The disclosure relates generally to the field of diagnostic imaging using structured light and more particularly relates to a method for automatic capture of fringe pattern images for three-dimensional imaging of the surface of teeth and other structures.

BACKGROUND

Fringe projection imaging uses patterned or structured light to obtain surface contour information for structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining images that provide additional measurements at the new locations, is typically applied as part of fringe projection imaging, used in order to complete the contour mapping of the surface and to increase overall resolution in the contour image.

Fringe projection imaging and other patterned light imaging techniques have been used effectively for surface contour imaging of solid, highly opaque objects and have been used for characterizing the surface contours for some portions of the human body and for obtaining detailed data about skin structure. However, a number of technical obstacles complicate effective use of patterned light imaging of the tooth. One particular challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

From an optics perspective, the structure of the tooth itself presents a number of additional challenges for fringe projection imaging. As noted earlier, light penetrating beneath the surface of the tooth tends to undergo significant scattering within the translucent tooth material. Moreover, reflection from opaque features beneath the tooth surface can also occur, adding noise that degrades the sensed signal and thus further complicating the task of tooth surface analysis.

One corrective measure that has been attempted to make fringe projection workable for contour imaging of the tooth is application of a coating that changes the reflective characteristics of the tooth surface itself. Here, to compensate for problems caused by the relative translucence of the tooth, a number of conventional tooth contour imaging systems apply a paint or reflective powder to the tooth surface prior to surface contour imaging. For the purposes of fringe projection imaging, this added step enhances the opacity of the tooth and eliminates or reduces the scattered light effects noted earlier. However, there are drawbacks to this type of approach. The step of applying a coating powder or liquid adds cost and time to the tooth contour imaging process. Because the thickness of the coating layer is often non-uniform over the entire tooth surface, measurement errors readily result. More importantly, the applied coating, while it facilitates contour imaging, can tend to mask other problems with the tooth and can thus reduce the overall amount of information that can be obtained. Even where a coating or other type of surface conditioning of the tooth is used, however, results can be disappointing due to the pronounced contours of the tooth surface.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but requiring application of a fluorescent coating for operation. Similarly, U.S. Pat. No. 6,885,464 entitled "3-D Camera for Recording Surface Structures, in Particular for Dental Purposes" to Pfeiffer et al. discloses a dental imaging apparatus using triangularization but also requiring the application of an opaque powder to the tooth surface for imaging. U.S. Pat. No. 6,885,464 to Pfeiffer et al. describes an intraoral camera that provides a group of light beams for imaging. Patent application WO 2011/145799 by Lim describes a 3-D scanner using scanned laser light.

Among difficulties that have hampered design and development of suitable imaging apparatus for contour imaging of the teeth is the need for accurate and precise spatial registration when using patterned light. This requires addressing logistical problems that relate to locating the camera at a desired position within the mouth of the patient and holding the camera still, at the desired position, for the time needed to capture the patterned light image or images. In some cases, two or more still images must be captured with the tooth and camera in the same fixed positions relative to each other.

Thus, it can be seen that there is a need for improved methods for providing still image capture for surface contour characterization using an intra-oral camera.

SUMMARY

It is an object of the present invention to advance the art of dental imaging for surface contour characterization. It is a feature of the present invention that it uses information from video image frames in order to detect relative movement of the camera and imaged tooth and can trigger contour image capture based on this detection.

Among advantages offered by the apparatus and method of the present invention are automated image capture for contour imaging without added camera components and improved imaging of tooth surfaces.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to one aspect of the disclosure, there is provided a method for obtaining a contour image of a tooth, the method executed at least in part by a computer and comprising:

detecting movement of an intra-oral camera by:
(i) acquiring a first video image frame that includes the tooth and processing the first video image frame to detect one or more edges of the tooth in the first video image frame;
(ii) acquiring a second video image frame that includes the tooth and processing the second video image frame to detect the one or more edges of the tooth in the second video image frame;
(iii) comparing corresponding edge locations between the first and second processed video image frames; and projecting a fringe pattern illumination onto the tooth from the camera and capturing and storing one or more still images of the fringe pattern according to the detected camera movement.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DETAILED DESCRIPTION OF EXEMPLARY EMBODIMENTS

Figure 1A:
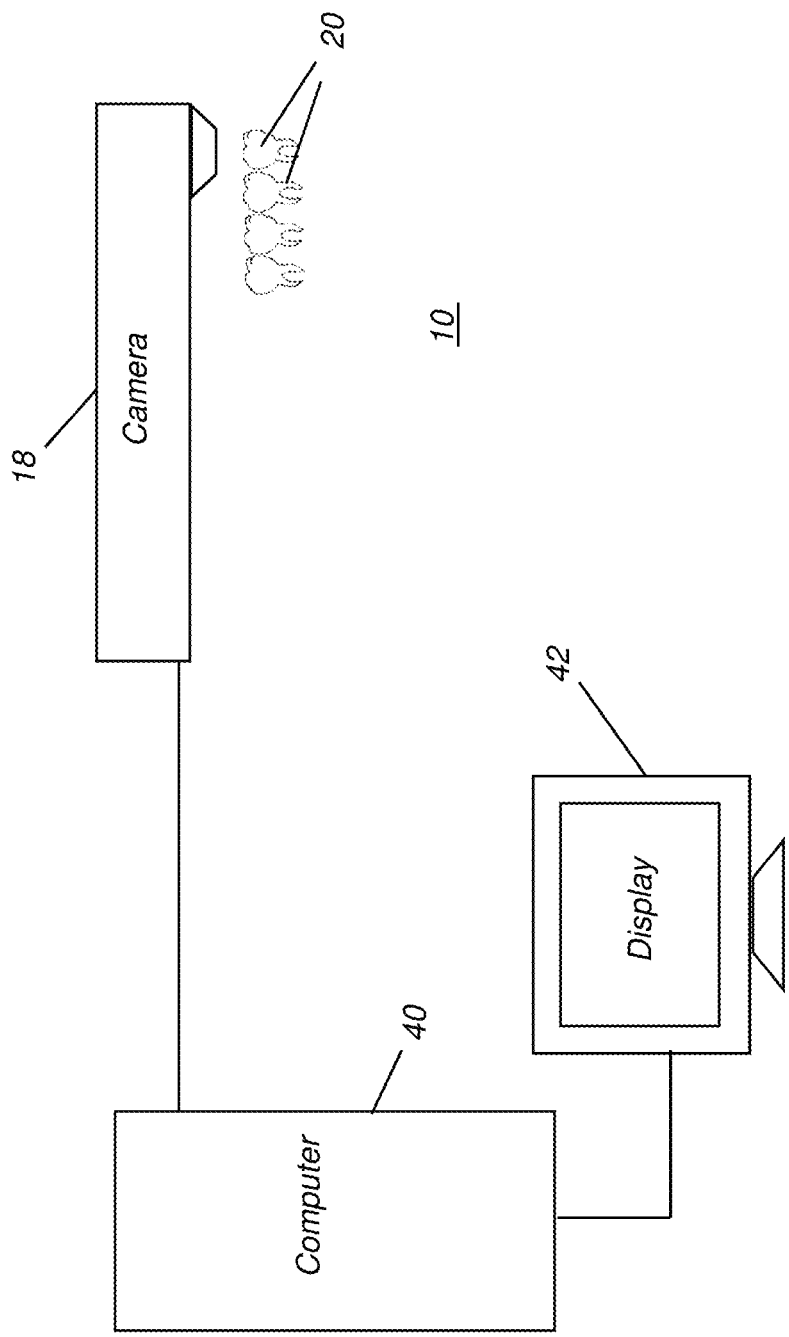
FIG. 1A shows an intra-oral imaging apparatus for contour imaging of teeth.
Figure 1B:
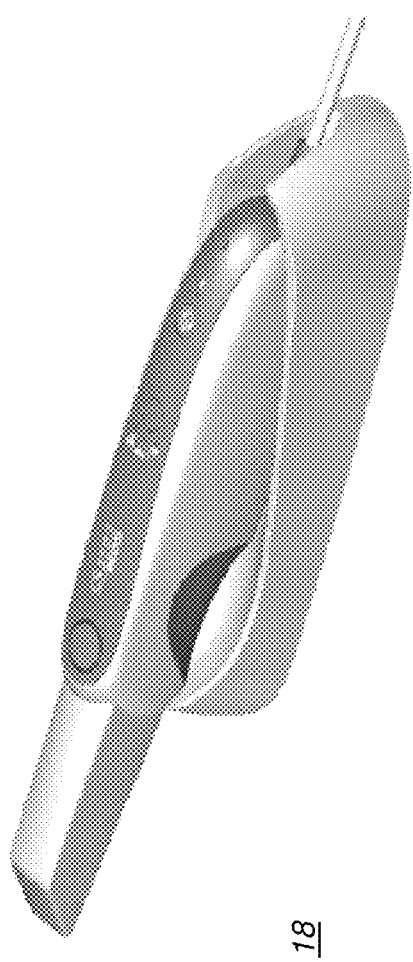
FIG. 1B is a perspective view that shows an intra-oral camera having video and contour imaging capability.

The following is a detailed description of the preferred embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "fringe pattern illumination" is used to describe the type of structured illumination that is used for fringe projection imaging or "contour" imaging that characterizes tooth shape. The fringe pattern itself can include, as patterned light features, one or more lines, circles, curves, or other geometric shapes that are distributed over the area that is illuminated and that have a predetermined spatial and temporal frequency. One exemplary type of fringe pattern that is widely used for contour imaging is a pattern of evenly spaced lines of light projected onto the surface of interest.

In the context of the present disclosure, the terms "structured light image" and "contour image" are considered to be equivalent and refer to the image that is captured during projection of the light pattern that is used for characterizing the tooth contour.

Two lines of light, portions of a line of light, or other features in a pattern of structured illumination can be considered to be substantially "dimensionally uniform" when their line width is the same over the length of the line to within no more than +/−15 percent. As is described in more detail subsequently, dimensional uniformity of the pattern of structured illumination is used to maintain a uniform spatial frequency.

In the context of the present disclosure, the term "optics" is used generally to refer to lenses and other refractive, diffractive, and reflective components used for shaping a light beam.

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

As was noted earlier in the background section, conventional approaches for fringe projection imaging often yield disappointing results for characterizing tooth structure due to movement by the practitioner who is performing image capture or due to movement by the patient. In the context of the present disclosure, relative movement of the camera relative to the tooth or teeth being imaged is termed "camera movement" for simplicity; it is understood that the phrase "camera movement" refers to relative movement between camera and imaged object and can, in some cases, occur due to movement of the patient, and hence of the object tooth, rather than due to movement of the camera. When the camera is stationary or fixed, there is considered to be no camera movement. As is described subsequently, a threshold value is computed in order to determine whether or not perceived camera movement exceeds a predetermined tolerance or threshold. In practice, when a camera is stationary or fixed, structured light images of the tooth can be obtained and contour imaging of the tooth features can be computed.

Apparatus and methods of the present invention address the problem of camera movement detection and provide exemplary methods that allow automated image capture when it can be determined that the relative position of the imaged tooth and camera are substantially fixed. Embodiments of the present disclosure address the problem of detecting camera movement for an intra-oral camera that is configured to capture both video and still images, as is described in more detail subsequently.

Referring to FIG. 1A, there is shown an intra-oral imaging apparatus 10 for video and contour imaging of one or more teeth 20 that includes an intraoral camera 18 the form of a probe. The camera 18 communicates, over a wired or wireless data communication channel, with a computer 40 that obtains the images from the projected fringe pattern. Computer 40 processes the images and provides output image data that can be stored as a data file and displayed on a display 42.

Figure 1C:
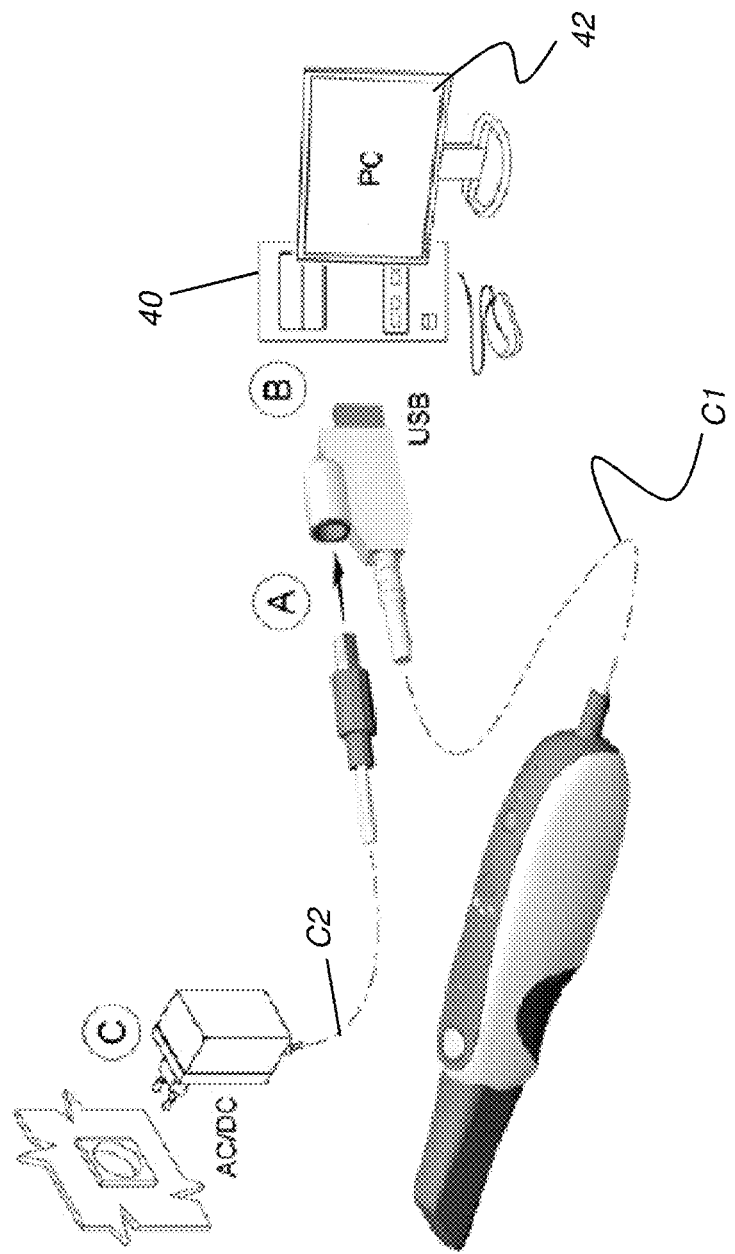
FIG. 1C is a perspective view showing the intra-oral camera and interconnection with related components of the intra-oral imaging apparatus.

The perspective view of FIG. 1C shows intra-oral camera 18 designed for handheld use and having video and contour imaging capability. In the embodiment shown, camera 18 has a data cable C1 with a power cable C2 connection. Data cable C1 connects to computer 40 for image processing, storage, and display functions.

Figure 1D:
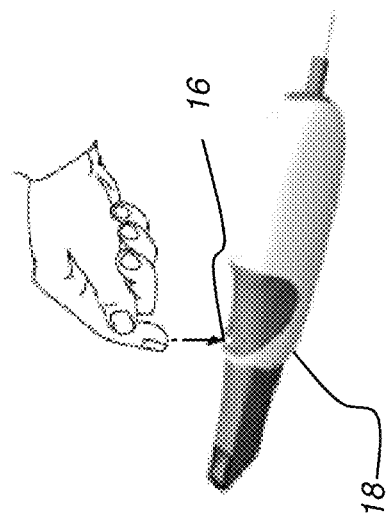
FIGS. 1D and 1E show operator selection of manual or automatic mode for contour imaging.
Figure 1E:
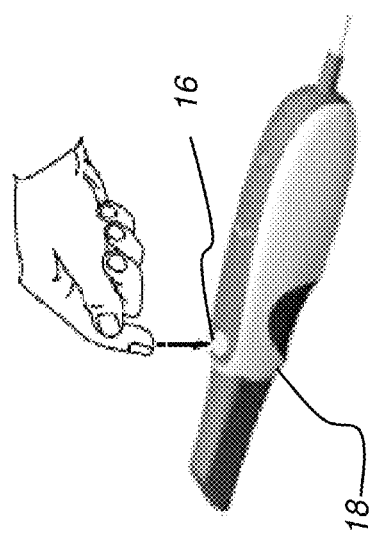

FIGS. 1D and 1E show operator selection of an optional switch 16 that is actuable for selecting manual or automatic mode for contour imaging. In automatic mode, the camera continually captures structured light images, without specific instruction from the operator. In manual mode, the operator provides an instruction for each contour image capture; otherwise, the structured light illumination and capture is not initiated.

Figure 2A:
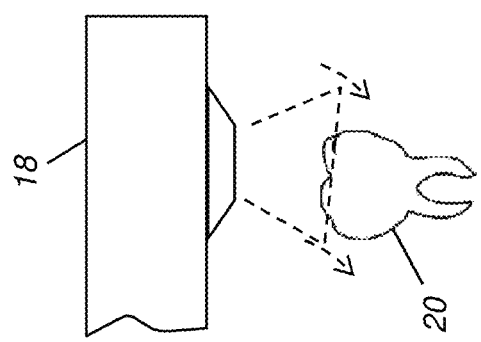
FIG. 2A shows using the camera to obtain a fringe pattern for contour imaging of teeth.
Figure 2A:
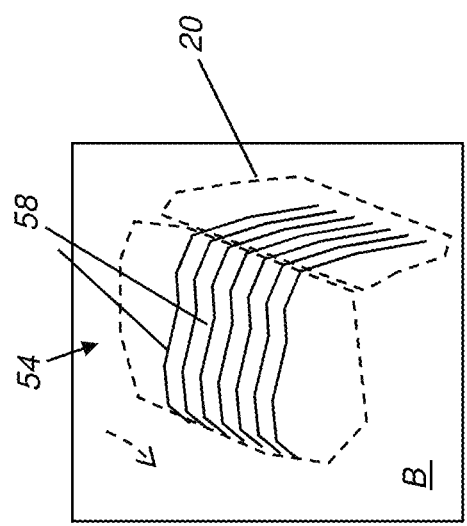

As shown in FIG. 2A, camera 18 includes a projector that scans an emitted pattern 54 of lines 58 or other features along the surface of tooth 20 as shown in an inset B. Camera 18 then captures the image periodically during the scan in order to obtain one or more images that can be combined to show contour information about the tooth surface. The contour imaging components of the present disclosure can be incorporated in a camera that also provides standard video imaging using reflectance images or other type of imaging, such as fluorescence imaging.

Figure 2B:
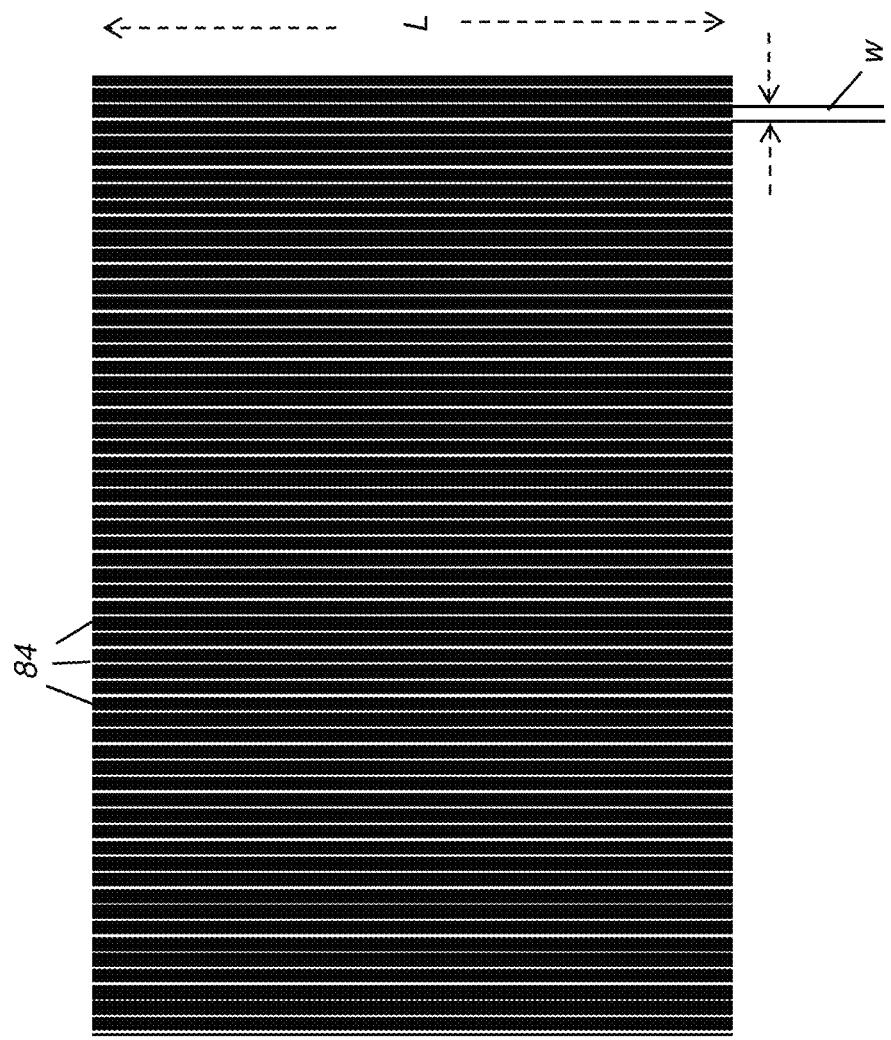
FIG. 2B is a plan view that shows a projected pattern.

The scan pattern, such as the pattern of evenly spaced, parallel lines 84 of light shown in FIG. 2B, can be generated in any of a number of ways. According to an embodiment of the present disclosure, pattern 54 is formed by scanning a light beam from a single laser diode over a portion of the two-dimensional surface. One scan moves the point of light in the direction of length L; another scan increments the position of the light source for the next scan line by a width distance w that is orthogonal to length L. The scan can be continuous, provided as long as camera 18 is energized, with the scanned pattern captured only when instructed by the operator or when initiated automatically by the imaging system. According to an alternate embodiment of the present disclosure, the scan is generated and captured only when camera movement ceases, even when initiated by operator command entry. Spectral characteristics of the scanned light may be perceptible within the video image where visible light is used for scanning. According to an alternate embodiment of the present disclosure, light outside the visible range is used for contour scanning. One or more images may need to be captured and combined in order to obtain the complete pattern of scanned patterns for a particular tooth, such as the pattern of scanned lines in FIG. 2B.

Figure 2C:
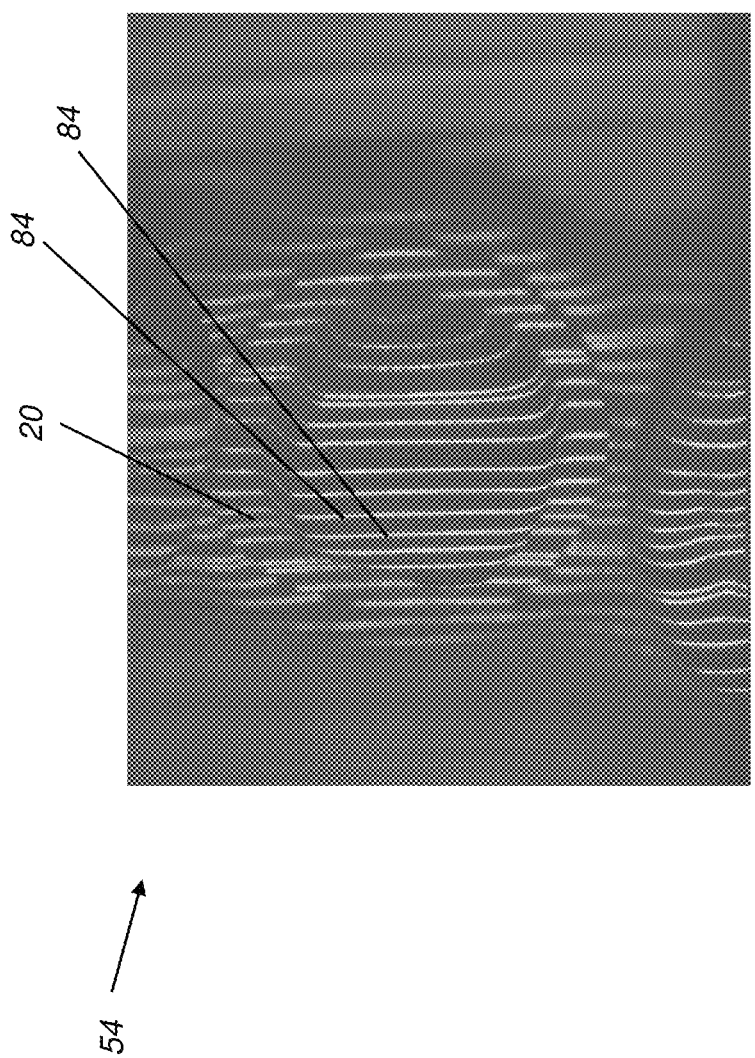
FIG. 2C shows a projected pattern on a model of a tooth.
Figure 2D:
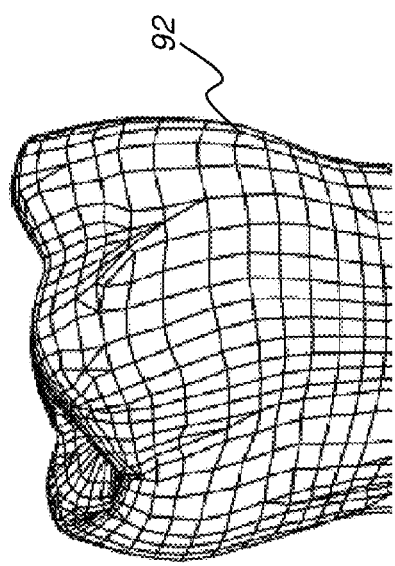
FIG. 2D shows an exemplary tooth surface computed using fringe pattern results.

Once the needed images of the scan pattern are acquired, the contour image can be formed, using computation techniques well known to those skilled in the surface imaging arts. FIG. 2C shows a projected pattern 54 of lines 84 on a model of tooth 20. By way of example, FIG. 2D shows a contour image 92 formed using pattern of parallel lines of light.

Figure 3:
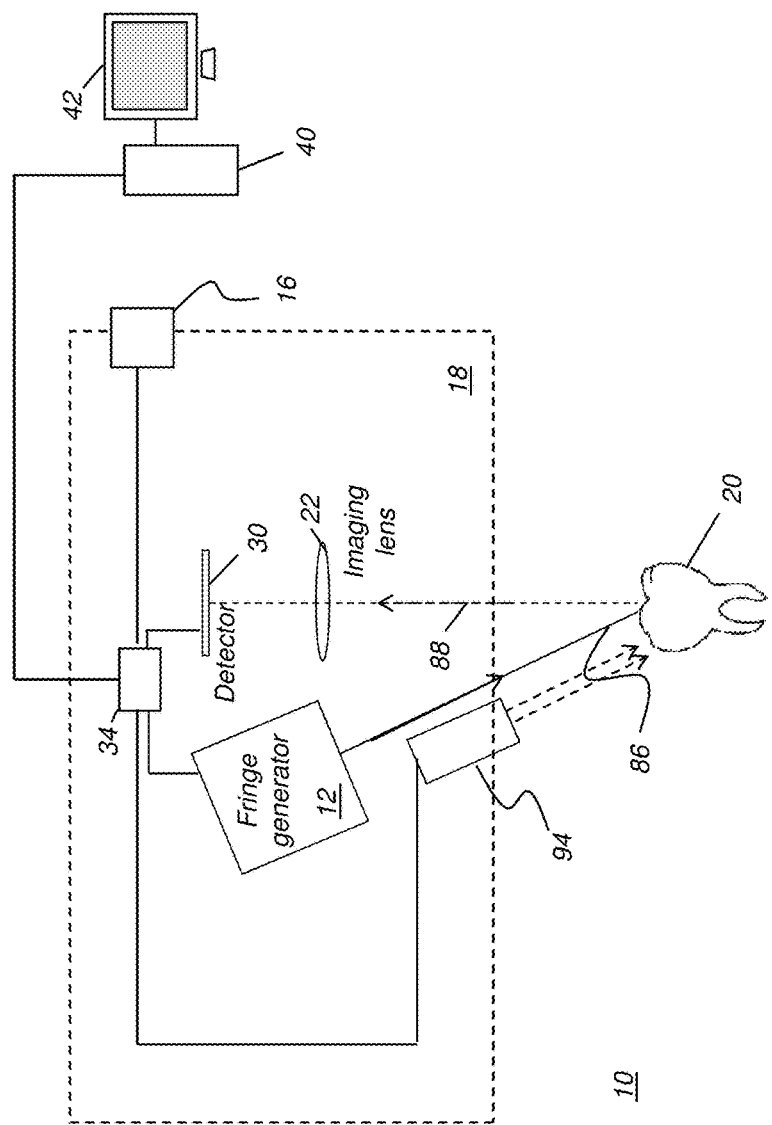
FIG. 3 is a schematic block diagram that shows components of an imaging apparatus for video and contour imaging.

Referring to the schematic block diagram of FIG. 3, there is shown in more detail an embodiment of an intra-oral imaging apparatus 10 for obtaining surface contour information from a tooth 20 using structured light illumination. In camera 18, a fringe pattern generator 12 is energized to form the structured light as a fringe pattern illumination and project the structured light thus formed as incident light toward tooth 20 having a beam direction along an illumination path 86. The fringe pattern illumination may be from a laser, advantageous for providing a narrow beam of coherent light. The laser may be a laser diode. Alternatively, the fringe pattern illumination is from a light emitting diode (LED) or other solid-state light source, using a spatial light modulator such as a micromirror array, liquid crystal device (LCD) or other light modulator. The patterned light is scanned along the tooth 20 surface. Light reflected and scattered from tooth 20 is provided to a detector 30, through an imaging lens 22. Detector 30 is disposed along a detection path 88, at the image plane of imaging lens 22. Detector 30 can be used to obtain both video images and structured light images. A control logic processor 34 accepts feedback information from detector 30 and, in response to this and other data, is actuable to effect the operation of pattern generator 12 such as to change the position of the projected image and to capture the image periodically as described in more detail subsequently.

In the embodiment of the present disclosure shown in FIG. 3, pattern generator 12 and an illumination source 94 have substantially parallel output axes along illumination path 86. Optional operator switch 16 enables the mode setting to be adjusted for manual or automatic, as described in more detail subsequently.

Functions of control logic processor 34 for fringe projection imaging include controlling generation of the fringe pattern from fringe generator 12 and triggering of detector 30 to capture images with appropriate timing for contour imaging. Control logic processor 34 can be a computer, microprocessor, or other dedicated logic processing apparatus that executes programmed instructions. Control logic processor 34 is in signal communication with computer 40 that has a display 42. Computer 40 is in signal communication with display 42 for display of video and contour image content for tooth 20.

Computer 40 may perform at least some portion of the image processing functions that utilize the data obtained by detector 30 and control logic processor 34 to provide images showing the surface contour and features of tooth 20. It should be noted that various control logic and imaging functions can be performed by either control logic processor 34 or computer 40 or can be shared between these control logic devices. For example, computer 40 may perform the image analysis functions for movement detection and provide the movement signal or signals that indicate whether or not fringe projection imaging can proceed. Additional computer devices can alternately be used to support various computational functions for contour analysis and display.

Figure 4:
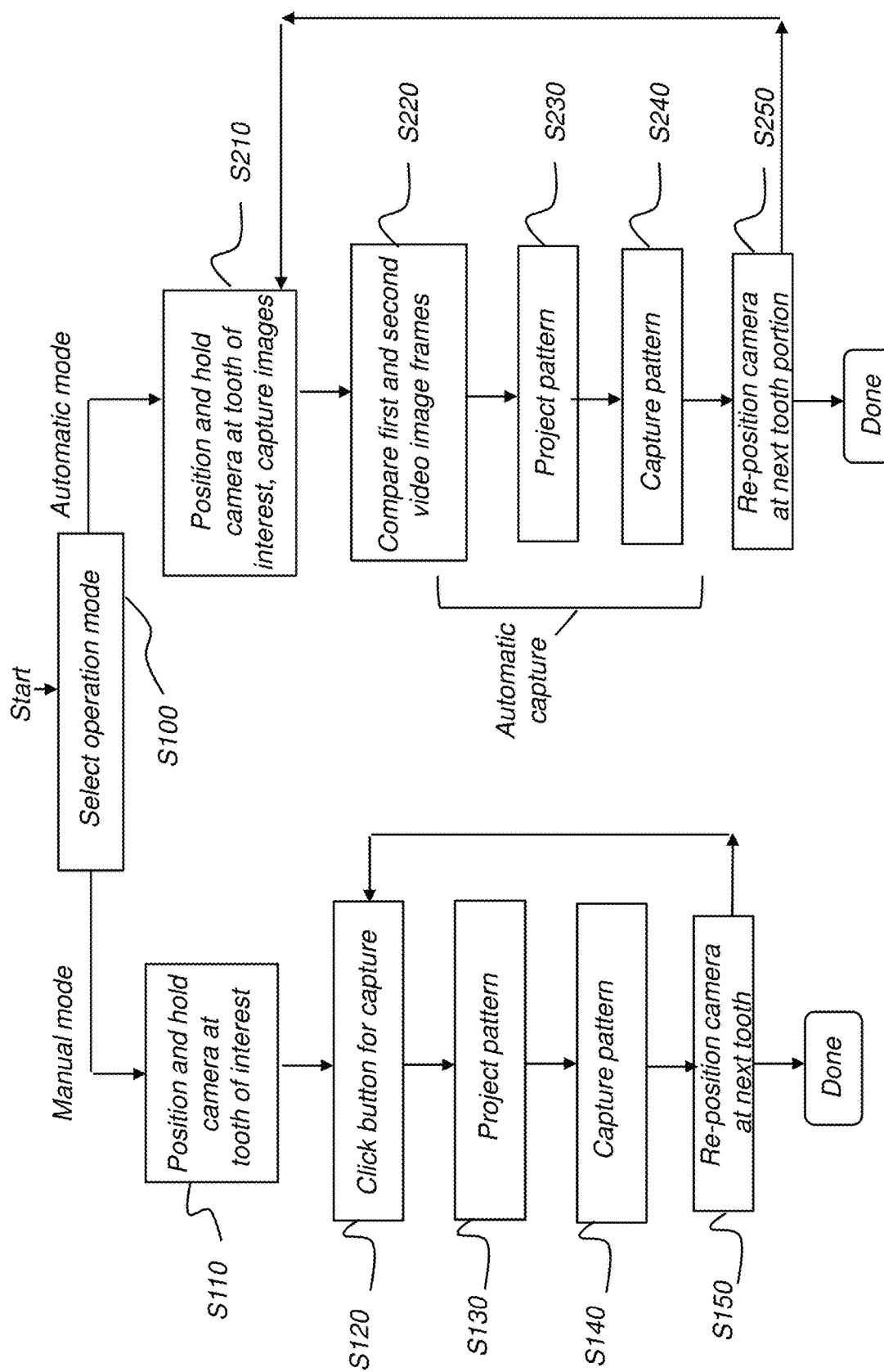
FIG. 4 is a logic flow diagram that shows steps for manual and automatic modes of intra-oral camera operation.

The logic flow diagram of FIG. 4 shows operation steps for manual and automatic modes of intra-oral camera operation for contour imaging. In a selection step S100, the operator makes a mode selection that determines the mode in which contour images are obtained. Referring back to the block diagram of FIG. 3, mode selection may be made on using switch 16. The operator selects either manual mode or automatic mode. In manual mode, a positioning step S110, the operator positions the camera near the tooth (or teeth) of interest for image acquisition. In a capture initiation step S120, the operator enters an instruction for capture of a contour image, such as by clicking a button or control on the intra-oral camera. In response, the camera executes a projection step S130 and projects the structured light pattern onto the tooth surface, then executes a capture step S140 to acquire an image of the projected pattern. The operator repositions the camera to repeat the sequence for additional image acquisitions for the current tooth of interest or for another tooth in a reposition step S150. Steps S120, S130, S140, and S150 are repeated as needed.

The right side of FIG. 4 shows the alternate sequence of operation for automatic mode. A positioning step S210 is executed as the operator positions the camera. Video images are continuously acquired and displayed during positioning step S210. Two successive video image frames (e.g., most recent and/or sequential) are compared in a frame comparison step S220 to determine the relative amount of camera movement, as described for example, in more detail subsequently. Operation proceeds when the camera is ascertained to be still, in fixed position with respect to the teeth or tooth of interest, according to a movement signal from control logic processor 34 or, alternately, from computer 40 (FIG. 3). A structured light pattern is projected in a projection step S230 and the image is immediately captured in a capture step S240. To continue the image acquisition for contour imaging, a reposition step S250 is executed, in which the operator moves the camera for positioning to an alternate portion of the current tooth of interest or to a different tooth or teeth. Steps S210, S220, S230, S240, and S250 are repeated as needed.

The structured light pattern can include a set of contour images with a varying fringe pattern illumination taken from a single position of the intra oral camera for a portion of the tooth of interest. For example, the set of contour images can be used to generate a single 3D view of the portion of the tooth of interest corresponding to the set of contour images. In one embodiment, the entire set of contour images can be taken while the camera remains still (e.g., step S220 operations) or the single 3D view of the portion of the tooth is preferably not generated. In one embodiment, multiple single 3D views of the portion of a tooth are used to generate the exemplary tooth surface shown in FIG. 2D.

Figure 5:
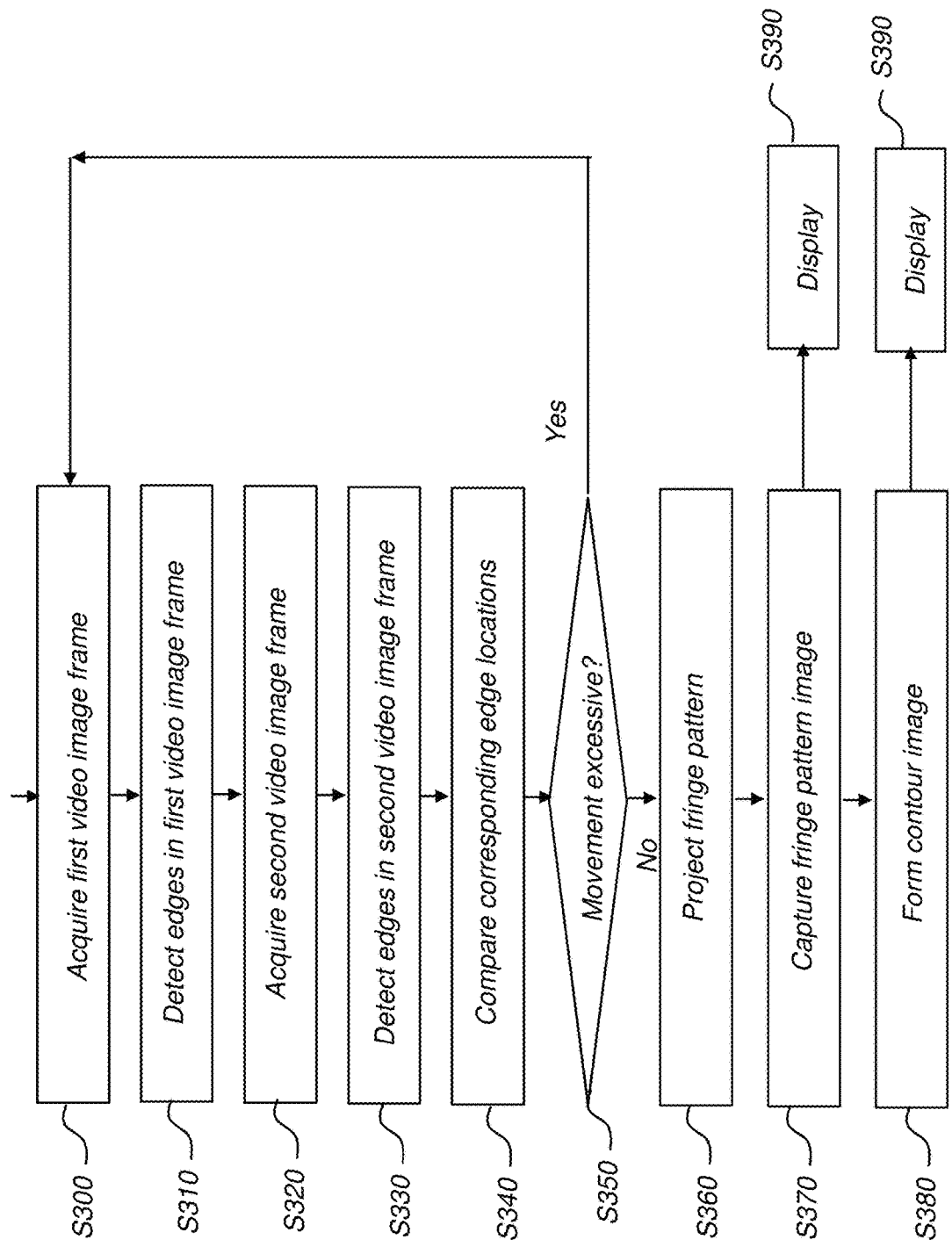
FIG. 5 is a logic flow diagram that shows automatic motion detection and fringe pattern image capture according to an embodiment of the present disclosure.

With reference to FIG. 4, the automatic mode of steps S210, S220, S230, S240, and S250 uses video image data in order to determine whether or not the camera is reasonably stationary, in position for accurate contour imaging. The logic flow diagram of FIG. 5 shows exemplary data handling steps for automatic motion detection and fringe pattern image capture in automatic mode, according to an embodiment of the present disclosure. In a video image capture step S300, the intra-oral camera acquires a first video frame. Tooth edges are detected in an edge detection step S310. In a second video image capture step S320, a subsequent video frame (e.g., the next video frame) is acquired. Tooth edges for this second video frame are detected in an edge detection step S330. A comparison step S340 then compares corresponding edge locations between the first and second video image frames. In a decision step S350, this comparison determines whether or not the camera is moving. Excessive camera movement can prevent contour image projection and capture in subsequent steps. When there is excessive movement, activity returns to step S300 to repeat the image acquisition and assessment. If, on the other hand, comparison step S340 indicates that the camera is substantially in stationary position, then decision step S350 provides this result for execution of a projection step S360 that projects a structured light pattern onto the tooth of interest. A capture step S370 captures one or more images of the projected structured light pattern, which is optionally displayed in a display step S390. A contour image generation step S380 then forms a contour image of the tooth using the captured fringe pattern images. The contour image is displayed in display step S390.

According to an alternate embodiment of the present disclosure, automatic mode image capture includes some further interaction with the operator of camera 18. If the first and second video image frames show no significant camera movement in step S220, the operator instructions for pattern projection and image capture are enabled, so that pattern projection step S230 and capture step S240 execute. The operator obtains image capture at the press of a button. However, if there is too much camera 18 movement, one or both of steps S230 and S240 may be disabled until perceived camera movement decreases to below a predetermined threshold.

In one embodiment, the structured light pattern in projection step S360 can include a set of contour images (e.g., 4, 8, or more) with a constant or varying fringe pattern illumination taken from a single orientation the tooth or interest (e.g., or a portion of the tooth of interest) that are captured in capture step S370. For example, the set of contour images can be used to generate in contour image generation step S380 a single 3D view of the portion of the tooth of interest corresponding to the set of contour images that can be displayed in display step S390. In one embodiment, one or more or the captured entire set of contour images can be displayed in display step S390. In one embodiment, multiple single 3D views of the portion of a tooth (or teeth) are used to generate such exemplary tooth surfaces shown in FIG. 2D.

It should be noted that motion detection using the technique described with respect to FIG. 5 works best when the first and second video image frames that are compared are temporally adjacent, that is, when the second video image frame is captured immediately following the first video image frame. Alternately, the second video frame can be at least within no more than three video frames of the first video image frame.

As the position of intra-oral camera 18 changes, the relative position(s) of the needed fringe projection image(s) for contour characterization may also change. Camera 18 software may detect position change and, depending on the direction and magnitude of movement, compensate for some amount of detected position change by shifting the position of the projected fringe pattern illumination for subsequent image capture. Techniques for measuring spatial position change and methods for adjusting the position of a projected light pattern according to a detected position change are known to those skilled in the contour imaging arts. Techniques routinely used for image deformation can be applied to this problem, for example.

Figure 6:
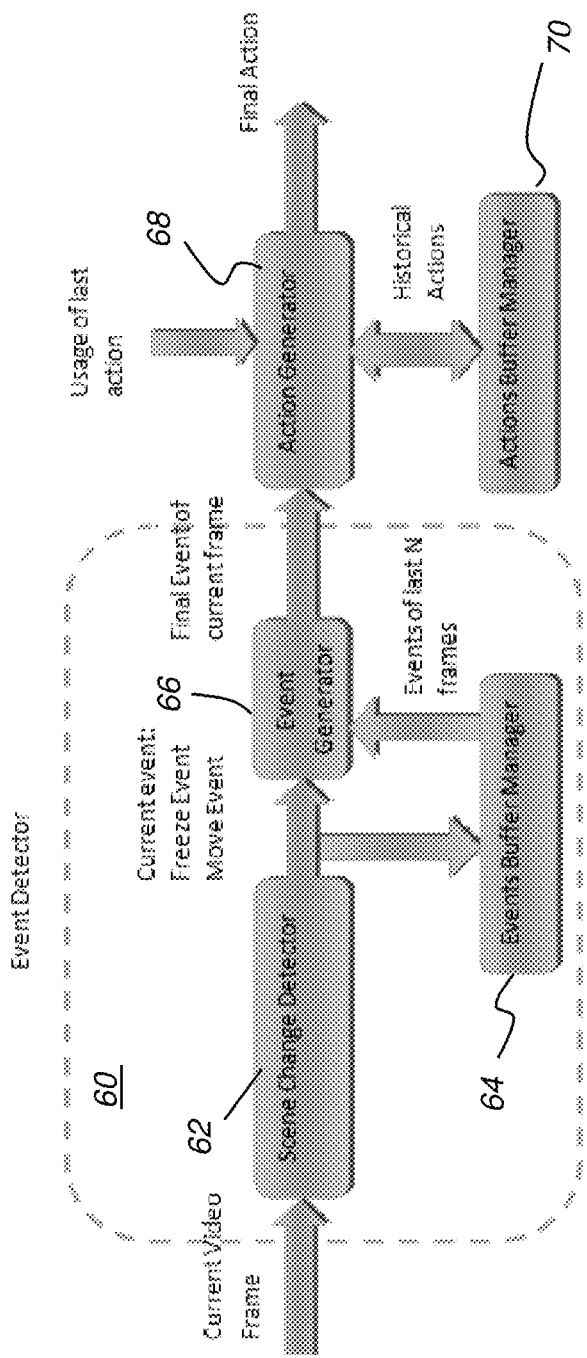
FIG. 6 is a flow diagram that shows functional components used in processing video image content to support structured light image capture.

The logic flow diagram of FIG. 6 shows functional components of software supporting intra-oral camera 18, wherein the functional components are used in processing video image content to support structured light image capture. In an event detector 60, a scene change detector 62 samples a video frame, processes it to detect edges, and compares it against its preceding video frame to determine whether or not the camera is stationary or moving. Results go to an event buffer manager 64 that stores each processed frame and to an event generator 66 that indicates a stationary or moving state. An action generator 68 generates one or more final action instructions based on the current state of the software logic. An actions buffer manager 70 records information about the contour imaging acquisition.

Figure 7:
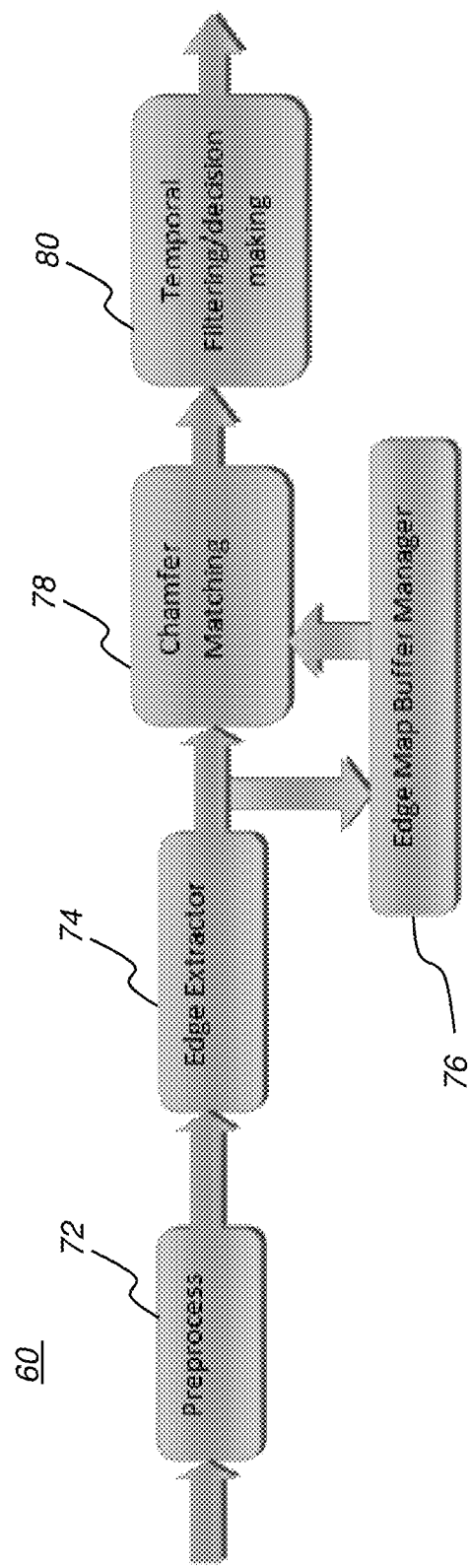
FIG. 7 shows the relationship of functional components for determining camera movement.

FIG. 7 shows components of event detector 60 in greater detail. In a preprocessor 72, each input video frame is filtered and resized for more efficient processing, such as by scaling to a lower resolution. An edge extractor 74 then processes the scaled, processed video frame to detect edges. Edge detection is well known in the image processing arts and may, for example, use any of a number of digital filters that highlight edge details. Among algorithmic approaches to edge detection are so-called Canny edge detection, Gabor filters, and various methods that analyze and process image gradients using differential geometry, for example. According to an embodiment of the present disclosure, a 2-D deviation of Gaussian spatial filtering can be used to derive a binary edge map for each image frame.

Continuing with the processing shown in FIG. 7, a chamfer matching process 78 then compares edge detection for each image and the image immediately preceding, obtained from an edge map buffer manager 76, in order to estimate camera movement. A temporal filtering/decision process 80 then determines whether the camera position is stationary or whether there is appreciable camera movement. Temporal filtering may use an infinite impulse response (IIR) filter, for example.

Figure 8B:
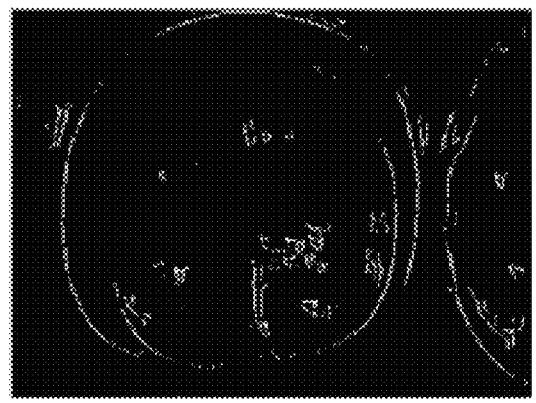
FIG. 8B shows an exemplary edge map generated from the filtered tooth image.
Figure 8A:
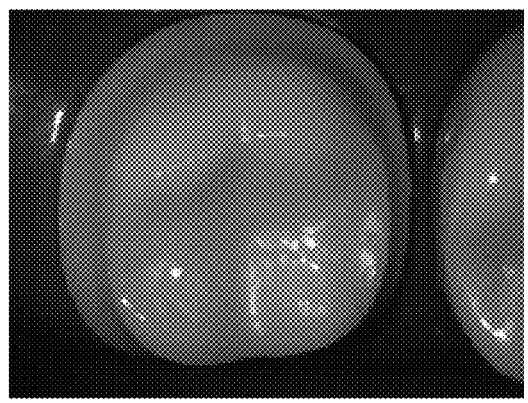
FIG. 8A shows an exemplary filtered tooth image.

FIG. 8A shows an exemplary filtered tooth image 56, prior to preprocessing and edge detection. FIG. 8B shows an exemplary edge map 52 generated from the filtered tooth image.

Chamfer matching is a well known technique for providing a metric for edge correlation between images. Given two edge images of the same subject, chamfer matching uses various techniques to find the best alignment between the respective edge maps. Efficient and robust for edge alignment, chamfer matching can reduce or minimize a generalized distance between two sets of edge points on a reference image and a test image. A reference on chamfer matching is given by Ming-Yu Liu, Oncel Tuzel, Ashok Veeraraghavan, and Rama Chellappa, in a paper entitled "Fast Directional Chamfer Matching", *Proceedings of the IEEE Conference on Computer Vision and Pattern Recognition (CVPR'10)*, San Francisco, Calif. June 2010, pp. 1696-1703.

Figure 9:
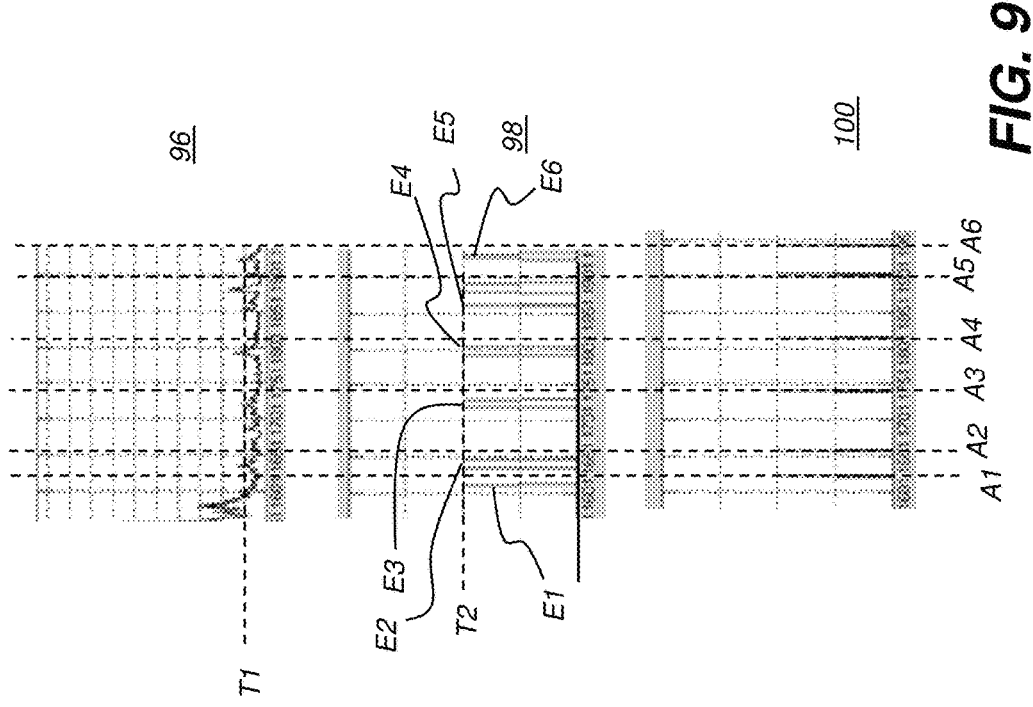
FIG. 9 shows timing relationships for comparison of edge maps to determine movement.

The aligned graph portions of a difference map 96, and related graphs 98, and 100 given in FIG. 9 show timing relationships for comparison of edge maps to determine movement. The graphs show edge detection and related processing for an example using a sampling of more than 300 successive video frames. For this processing, a current video frame and its preceding video frame are compared. According to an embodiment of the present disclosure, difference map 96 represents differences in the average Euclidean distance between corresponding pixels in identifiable edge features or between features in adjacent images. When this distance exceeds a predetermined threshold T1, excessive camera movement is indicated; contour image projection and capture is thus suspended until the average distance drops to below threshold T1. High spikes in the curve represent the high difference between successive frames, which means rapid movement of camera is happening in scenes of normal teeth. After temporal filtering on the chamfer matching of the current frame by an IIR filter, the filtered chamfer matching value is compared with a fixed threshold so as to generate a binary decision, as shown in graph 98. If the matching value exceeds the threshold, the decision is 'Moving'; otherwise, the decision is 'Static'. The decisions for the current frame and for the previous N frames are summed. If enough frames would generate 'Moving', the final event assigned to the current frame is 'Event-Moving'; otherwise the final event that is assigned is 'Event-Static'.

Graph 98 converts the difference activity of difference map 96 to a binary representation, as events E1, E2, E3, E4, E5, and E6, for example. Thus, values of these events at threshold T2 indicate periods of active camera movement. When the graph 98 value is at zero, the camera position is considered to be stationary, so that contour imaging would be allowed. The event transition is shown in graph 100 that shows final actions A1, A2, A3, A4, A5, and A6, for example. Final actions indicate times at which image capture can be obtained, based on corresponding computations reflected in difference map 96 and graph 98.

The final event of the current frame is input to an action generator 68, a process which integrates the current event and previous events to decide whether or not to capture the image. For an 'Event-Static' event, indicating a stationary camera condition, a 'Capture Action' is generated. When a sufficient number of continuous frames output 'Capture Action', a 'Capture Action' is finally output for the current frame. The intra-oral camera is then triggered to project and capture contour images. In addition, if a previous 'Capture Action' has not generated a successful capture, other additional 'Capture Action' commands are output. The number of Capture Action events that are stored and related image handling parameters are predetermined for the camera and, alternately, may be varied according to imaging conditions or operator preference.

According to an alternate embodiment of the present disclosure, the image capture sequence includes logic for detecting patient movement during the scan imaging sequence. Movement detection can be performed in a number of ways, including by repeated projection and capture of the same image content during the imaging cycle, for example.

Based on the acquired images of the projected pattern 54, computer 40 then generates contour information for the tooth, as shown in the example of FIG. 2D.

Detectors 30 in embodiments described herein can be any of a number of types of image sensing array. Detector 30 can be a CMOS (complementary metal oxide semiconductor) imaging sensor or a CCD (charge-coupled device) sensor, for example. The camera optics can also include filters, polarizers, and other components in the projection or detection paths.

In one embodiment of the present invention, the imaging apparatus is packaged in the form of a hand-held probe that can be easily positioned within the patient's mouth with little or no discomfort.

The surface contour image that is obtained using the apparatus and methods of the present invention can be processed and used in a number of ways. Contour data can be displayed and can be input into a system for processing and generating a restorative structure or can be used to verify the work of a lab technician or other fabricator of a dental appliance. This method can be used as part of a system or procedure that reduces or eliminates the need for obtaining impressions under some conditions, reducing the overall expense of dental care. Thus, the imaging performed using this method and apparatus can help to achieve superior fitting prosthetic devices that need little or no adjustment or fitting by the dentist. From another aspect, the apparatus and method of the present invention can be used for long-term tracking of tooth, support structure, and bite conditions, helping to diagnose and prevent more serious health problems. Overall, the data generated using this system can be used to help improve communication between patient and dentist and between the dentist, staff, and lab facilities.

Advantageously, the apparatus and method of the present invention provide an intra-oral imaging system for 3-D imaging of teeth and other dental features without requiring the use of a special powder or application of some other temporary coating for the tooth surface. The system offers high resolution, in the 25-50 µm range in one embodiment.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for obtaining a contour image of a tooth, the method executed at least in part by a computer and comprising:
    detecting movement of an intra-oral camera using video images from a video imaging system in the intra-oral camera by:
       (i) acquiring a first video image frame that includes the tooth and processing the first video image frame to detect one or more edges of the tooth in the first video image frame;
       (ii) acquiring a second video image frame that includes the tooth and processing the second video image frame to detect the one or more edges of the tooth in the second video image frame;
       (iii) comparing corresponding edge locations between the first and second processed video image frames; and
    projecting a fringe pattern illumination onto the tooth from the camera and capturing and storing one or more still images of the fringe pattern when the detected camera movement is below a prescribed threshold.

2. The method of claim 1 wherein comparing corresponding edge locations comprises using a chamfer matching process.

3. The method of claim 1 further comprising displaying the captured one or more still images.

4. The method of claim 1 further comprising shifting the position of the projected fringe pattern illumination along the tooth surface and repeating the step of projecting the fringe pattern illumination and capturing and storing the one or more still images of the fringe pattern according to the detected camera movement.

5. The method of claim 1 further comprising forming and displaying a three-dimensional image of the tooth surface using the one or more still images of the fringe pattern.

6. The method of claim 1 further comprising accepting an operator instruction to project, capture, and store the one or more still images automatically.

7. The method of claim 1 further comprising the step of calculating what fringe pattern images are needed and automatically determining intra-oral camera position and capturing projection pattern images as the camera position is changed.

8. The method of claim 1 wherein the first video frame is temporally adjacent to the second video frame.

9. The method of claim 1 wherein comparing corresponding edge locations comprises scaling the first and second processed video image frames.

10. The method of claim 1 wherein the fringe pattern illumination includes laser light.

11. The method of claim 1 wherein comparing corresponding edge locations comprises computing at least one Euclidean distance value.

12. A method for obtaining a contour image of a tooth, the method executed at least in part by a computer and comprising:
    detecting intra-oral camera movement by:
       (i) acquiring a first video image frame that shows the tooth and processing the first video image frame to detect one or more edges of the tooth;
       (ii) acquiring a second video image frame that shows the tooth and processing the second video image frame to detect the one or more edges of the tooth;
       (iii) comparing corresponding edge locations between the first and second processed video image frames to output a movement signal;
    energizing a laser and projecting a fringe pattern illumination onto the tooth and capturing and storing one or more still images of the projected fringe pattern when the movement signal based on the detected intra-oral camera movement in the first and second processed video image frames indicates that the detected intra oral camera movement is below a prescribed threshold; and
    forming and displaying a three-dimensional image of the tooth surface using the one or more still images of the fringe pattern.

13. The method of claim 12 wherein comparing corresponding edge locations comprises using a chamfer matching process.

14. The method of claim 12 further comprising displaying the captured one or more still images.

15. The method of claim 12 wherein comparing corresponding edge locations comprises scaling the first and second processed video image frames.

16. A apparatus for imaging a tooth comprising: an intra-oral camera that has:
    (i) a detector that acquires image data for video images or fringe pattern images of the tooth;
    (ii) a switch actuable for enabling contour imaging of the tooth;
    (iii) a first illumination source to project light toward the tooth for the video images; and
    (iv) a fringe pattern generator that is energizable to scan a laser light beam onto the tooth for contour imaging, when a movement signal indicative of intra oral camera movement indicates that the intra oral camera movement is below a threshold;
    a computer that is in signal communication with the intra-oral camera for receiving the image data acquired by the detector and for generating a contour image of the tooth;
    a control logic processor, internal to the intra-oral camera or on the computer, wherein the control logic processor analyses video image data to provides the movement signal that is indicative of camera movement relative to the tooth; and
    a display that is in signal communication with the computer for display of the video and contour images.

* * * * *